(12) United States Patent
Sanders et al.

(10) Patent No.: US 7,671,325 B2
(45) Date of Patent: Mar. 2, 2010

(54) BIOLOGICAL AGENT SIGNATURE DETECTOR WITH AN OPTICAL FIBER CLADDING COMBINED WITH A BIO-INDICATOR

(75) Inventors: Glen A. Sanders, Scottsdale, AZ (US); Stephen F. Yates, Arlington Heights, IL (US); F. Stephen Lupton, Evanston, IL (US)

(73) Assignee: Honeywell International Inc., Morristown, NJ (US)

( * ) Notice: Subject to any disclaimer, the term of this patent is extended or adjusted under 35 U.S.C. 154(b) by 53 days.

(21) Appl. No.: 11/679,498

(22) Filed: Feb. 27, 2007

(65) Prior Publication Data

US 2008/0203281 A1 Aug. 28, 2008

(51) Int. Cl.
*G01J 4/00* (2006.01)
*G01N 21/25* (2006.01)
(52) U.S. Cl. ............................. 250/227.18; 250/227.23
(58) Field of Classification Search ................................
250/227.14–227.18, 227.23; 385/127, 12, 385/6, 31, 32; 356/437, 480, 477, 478, 481, 356/483; 436/164
See application file for complete search history.

(56) References Cited

U.S. PATENT DOCUMENTS

| 4,834,496 A | 5/1989 | Blyler, Jr. et al. |
| 4,846,548 A * | 7/1989 | Klainer ........................ 385/12 |
| 5,248,319 A | 9/1993 | Ekiner et al. |
| 5,591,250 A | 1/1997 | Stern et al. |
| 5,649,045 A | 7/1997 | Fjare et al. |
| 2003/0107739 A1 * | 6/2003 | Lehmann et al. ............. 356/437 |
| 2004/0218257 A1 * | 11/2004 | Chen et al. ................ 359/341.1 |
| 2005/0030540 A1 * | 2/2005 | Thornton ..................... 356/432 |
| 2005/0185681 A1 * | 8/2005 | Ilchenko et al. ................ 372/20 |
| 2006/0123884 A1 * | 6/2006 | Selker et al. ................ 73/24.02 |
| 2006/0227331 A1 * | 10/2006 | Vollmer et al. .............. 356/483 |

FOREIGN PATENT DOCUMENTS

WO WO 2005/113121 12/2005

OTHER PUBLICATIONS

N. B. McKeown, B. Ghanem, K. J. Msayib, P. M. Budd, C. E. Tattershall, K. Mahmood, S. Tan , D. Book, H. W. Langmi and A. Walton, Towards polymer-based hydrogen storage materials: engineering ultramicroporous cavities within polymers of intrinsic microporosity, Angew. Chem. Int. Ed., 2006, 45, 1804-1807.

(Continued)

*Primary Examiner*—Que T Le
*Assistant Examiner*—Jennifer Bennett
(74) *Attorney, Agent, or Firm*—Husch Blackwell Sanders Welsh & Katz

(57) ABSTRACT

A biological agent detector for detecting predetermined biological agents. The biological agent detector includes an optical fiber, a cladding that clads a length of the optical fiber and a bioindicator disposed within the cladding. The biological agent detector also includes a coherent light source that excites the optical fiber and a biological agent signature detector that detects the presence of a biological agent based upon a change in a resonance characteristic of the optical fiber caused by absorption of the predetermined biological agent into the cladding of the fiber.

20 Claims, 4 Drawing Sheets

OTHER PUBLICATIONS

P.M. Budd, B. Ghanem, K. Msayib, N. B. McKeown, C. Tattershall, A nanoporous network polymer derived from hexaazatrinaphthylene with potential as an adsorbent and catalyst support, J. Mater. Chem., 2003, 13, 2721-26.

NB McKeown, S. Hanif, K. Msayib, C. Tattershall, PM Budd, Porphyrin-based nanoporous network polymers, Chem. Commun., 2002, 2782-83.

PM Budd, NB McKeown, D. Fritsch, Free volume and intrinsic microporosity in polymers, J. Mater. Chem., 2005, 15, 1977-86.

PM Budd et al., Polymers of intrinsic microporosity (PIMs): robust, solution-processable, organic nanoporous materials, Chem. Commun., 2004, 230-31.

NB McKeown et al., "Polymers of Intrinsic Microporosity (PIMs): Bridging the Void between Microporous and Polymeric Materials," Chem. Eur. J., 2005, 11, 2610-20.

PM Budd et al., "Solution-Processed, Organophilic Membrane Derived from a Polymer of Intrinsic Microporosity," Adv. Mater., 2004, 16, 456-59.

PM Budd et al., "Gas Separation Membranes from Polymers of Intrinsic Microporosity," J. Membr. Sci., 2005, 251, 263-69.

NB McKeown, S. Makhseed, PM Budd, Phthalocyanine-based nanoporous network polymers, Chem. Commun., 2002, 2780-81.

N.B. McKeown et al., Towards Polymer-Based Hydrogen Storage Materials: Engineering Ultramicroporous Cavities within Polymers of Intrinsic Microporosity, Angew. Chem. Int. Ed. 2006, 45, 1804-07, Feb. 2006.

Y. Hirayama et al., Relation between Gas Permeabilities and Structure of Polyimides, in Polymer Membranes for Gas and Vapor Separation, B.D. Freeman, I. Pinnau, ed. (1999).

G. Houghham et al., Influence of Free Volume Change on the Relative Permittivity and Refractive Index in Fluoropolyimides, Macromolecules 29, 3453-56 (1996).

Y. Hirayama et al., Relation of gas permeability with structure of aromatic polyimides I, J. Membrane Sci. 111, 169-82 (1996).

Alexander Star, Tzong-Ru Han, Vikram Joshi, Joseph R. Stetter, Sensing with Nafion Coated Carbon Nanotube Field-Effect Transistors, Electroanalysis 2004, 16, No. 1-2. pp. 108-112.

* cited by examiner

BIOLOGICAL AGENT SIGNATURE DETECTOR WITH AN OPTICAL FIBER CLADDING COMBINED WITH A BIO-INDICATOR

FIELD OF THE INVENTION

The present invention generally relates to environment sensing, and more particularly, to optical systems and methods for detecting the presence of biological materials.

BACKGROUND OF THE INVENTION

In recent times, greater emphasis has been placed on national home security and detecting threats to populations. In particular, detecting or sensing the presence of undesired chemicals or biological material in the environment has become a priority, and a variety of detection devices have been developed in response thereto. One example is a chemical sensor that uses a multi-mode optical fiber having a core and a cladding. The cladding, or coating on the cladding, has optical properties which are altered in the presence of a predetermined material to be detected. The amount of light transmitted through the core of the optical fiber is a function of the change in optical properties of the cladding or coating interacting with the material to be detected.

One design consideration for conventional detection devices is with sensitivity. In general, for a particular detection device, more time is generally required to detect the presence of undesired materials at lower concentration levels.

Accordingly, it is desirable to provide a sensor for detecting the presence of chemical and/or biological agents with enhanced sensitivity while minimizing the detection time. In addition, it is desirable to provide a sensor for detecting the presence of multiple and different threats while minimizing the package size of the sensor. Furthermore, other desirable features and characteristics of the present invention will become apparent from the subsequent detailed description of the invention and the appended claims, taken in conjunction with the accompanying drawings and this background of the invention.

SUMMARY

The present invention is directed to a biological agent detector for detecting predetermined biological agents. The biological agent detector includes an optical fiber, a polymer or hygroscopic gel material that blends with or covalently attaches a bioindicator and clads, or coats, the length of the optical fiber; and a bioindicator disposed within the cladding, or coating. The biological agent detector also includes a coherent light source that excites the optical fiber, configured within an optical fiber resonator, and a biological agent signature detector that detects a biological agent by one of a number of methods. One such method can include covalently linking antibodies to the region near, or just outside the core of an optical fiber and detecting antigen binding via measurement of changes in refractive index or light loss. Such method can be based upon a change in a resonance characteristics of the optical fiber resonator caused by absorption of the predetermined biological agent into the porous cladding or coating of the fiber. The optical resonator's resonance characteristics are modified by changes in optical parameters of an adjacent medium (to the core) interacting with the evanescent light wave of light travelling in the core. The intensity of the light, extends into the cladding, or coating, but diminishes with a distance from the core region. The electric field of the light which extends into the cladding or coating (outside the core) is sometimes referred to as the evanescent field of the light.

The biological agent detector may function by causing changes of refractive index, or loss in the immediate vicinity of a gel-fiber surface interface. This change is then amplified by the effect it has on the resonance characteristics of the optical fiber resonator in which the optical fiber is a part of. This method is particularly convenient because it requires no radioactive, fluorescent or other labeling of the target biological molecule or the detecting agent. In the foregoing material it is recognized that the words "cladding" is intended to mean a cladding, or a coating, or both. That is, the bioindicator can be put in the immediate layer surrounding the core of the fiber, known as the "cladding" since the evanescent field of the lightwave extend into the cladding. Alternatively, there may be a "inner" cladding or a cladding used to ensure guidance of light within the core that is not embedded with the indicator. In this system, a "coating" with the indicator, or a coating that functions as an outer "cladding" with the indicator, is added to a fiber structure with a non-active cladding. In these cases, the coating, or coating that functions as an outer cladding must absorb the bio-agent, have a portion of the evanescent tail of the light extend into it, and have a optical properties to support the guidance of light within the core.

In the biological agent detector of the present invention, known bioindicators specific to the microorganism or biological material, i.e., contaminant, to be detected, can be utilized as the bioindicator which are embeddable in the cladding. The preferred biodetecting agents are believed to be monoclonal antibodies. Monoclonal antibodies have high specificity for binding between specific antigens present in the target biological agent. Similarly, the detector can utilize known polymers or hygroscopic gel materials in which the indicator system can be embedded into the polymer or gel that clads the optical fiber. The cladding with the embedded indicator preferably is sufficiently durable to remain clad to the fiber during normal handling, preferably has a refractive index, when hydrated, which is sufficiently different from that of the core of the fiber such that it will operate successfully as a cladding material, and preferably remains hydrated at temperatures between about 40° F. and about 100° F. and relative humidities between about 30% and 90%. Frequently, such hygroscopic polymers are crosslinked gel materials which swell in the presence of water. Examples of such polymers include crosslinked chitosan materials, polysaccharides, hydroxy substituted acrylate coatings, and Nafion®. Nafion® is a registered trademark of E.I. Du Pont de Nemours and Company, Wilmington, Del., USA, for membranes and dispersions.

Another group of polymers believed to be operable as cladding material in this invention are polymers which are porous, and have surface tensions high enough that they will wick and absorb water into the pores at normal humidities. The Kelvin equation can be used to define the pore diameters required at a given surface tension to absorb water at the relative humidities required by the conditions of operation. It will be understood by those skilled in the art that optimization of the properties of the cladding to tailor it to each application is desirable and within the skills of those in the art. Overly thick cladding coatings will result in delayed response, whereas too thin cladding coatings may not be durable.

Biosensors based on the affinity binding of analytes to specific bioreceptors immobilised on the surface of an optical transducer, such as surface plasmon resonance sensor, Long Period Grating coupler, resonant mirror, and various types of interferometers, are believed to be useful for realtime detection of analytes by means of measuring changes in refractive index or light diffusion without the use of additional labelled reagents. The concentration of the bioindicator preferably is tailored to the requirements of the optical fiber system. Further, for porous cladding systems, the cladding preferably has openings sufficiently large so that the microorganisms to be detected, which may be relatively large on the scale of the porous systems can penetrate the cladding to reach the monoclonal antibody bioindicator, which in turn is preferably within reach of the light passing through the optical fiber. The monoclonal antibody is believed to only bind with the specific biological target molecule, specific to the particular target microorganism or biological toxin. Monoclonal antibodies are not restricted to biomolecules and large organic molecules can also be expected to be targeted by utilizing haptenization during the production of specific monoclonal antibodies. In the presence of the biological agent, i.e., the biocontaminant, the fiber is expected to become more lossy, degrading the finesse of the fiber resonator, or the fiber's effective index of refraction changes (changing the resonator's free spectral range), each of which can be sensed as a measure of the dose of biocontaminant absorbed. The fiber within the sensor's resonator is expected to operate using total internal reflection where an evanescent field interacts with bound antibody immobilized in the Fiber cladding. The reaction between antibody and antigen is expected to alter the light transmission to be monitored in real time as a change in refractive index or loss, thereby eliminating the need for labeling antigen molecules.

It is also believed that photonic crystal fibers (PCF) can be utilized as the optical fiber in the detector, whereby the gel is introduced into holes in the cladding of the PCF. Because of the high surface tension of the hole geometry in the cladding, the gel will not wick out. Airborne gaseous biocontaminant molecules may be exposed to the gel through very small diameter pinholes that may be punched into the optical fiber through the cladding along the length of the fiber and intersecting the holes that are populated with gel.

DETAILED DESCRIPTION OF A PREFERRED EMBODIMENT

The following detailed description of the invention is merely exemplary in nature and is not intended to limit the invention or the application and uses of the invention. Furthermore, there is no intention to be bound by any theory presented in the preceding background of the invention or the following detailed description of the invention.

Apparatus and methods are provided for sensing one or more biological agents in an environment. In general, the apparatus comprises a resonator having an optical fiber coil with a cladding that is embedded with an indicator (e.g., a highly specific monoclonal antibody) that reacts to a predetermined biological agent. When an input light beam (e.g., from a light source) is supplied to the resonator and the input light beam is tuned to the resonance frequency of the optical fiber resonator, which contains a coil of the optical fiber, in one direction (e.g., a clockwise or a counter-clockwise direction of the optical fiber coil in the case of a ring resonator), a resonance lineshape is produced in the region of the resonance frequency, which is sensed by the light circulating through the resonator. With the agent to be detected absent from the environment, the resonance lineshape has a first (e.g., narrow) profile corresponding to a low energy loss of the light circulating in the resonator. In the case of a sensor that utilizes increased loss, the presence of the predetermined biological agent in the environment of the optical fiber coil, the indicator reacts with this agent and, as a result, a portion of the light circulating in the optical fiber coil is scattered or absorbed. The normally narrow, resonance lineshape changes to a wider, shallower profile. This change in resonance lineshape represents a greater energy loss resulting from the scattered light or absorbed light and thus, indicates the presence of the predetermined biological agent reacted with the monoclonal antibody indicator. Another loss-increase mechanism may be that the cladding index rises, causing the light inside the core to be more weakly guided, which will also reduce the resonator finesse. Multiple optical fiber coils may be multiplexed together in the sensor, forming multiple resonators, to simultaneously detect the presence of multiple biologic agents. The additional resonators may also be used to sense other secondary materials, whose presence may adversely bias the measurement of the primary material that is intended to be detected. In this way, cross-sensitivities of one resonator coil or indicator to a secondary material may be eliminated. This provides a clearer measurement of the primary material or eliminates the possibility of a false alarm that is caused by the secondary material.

Figure 1:
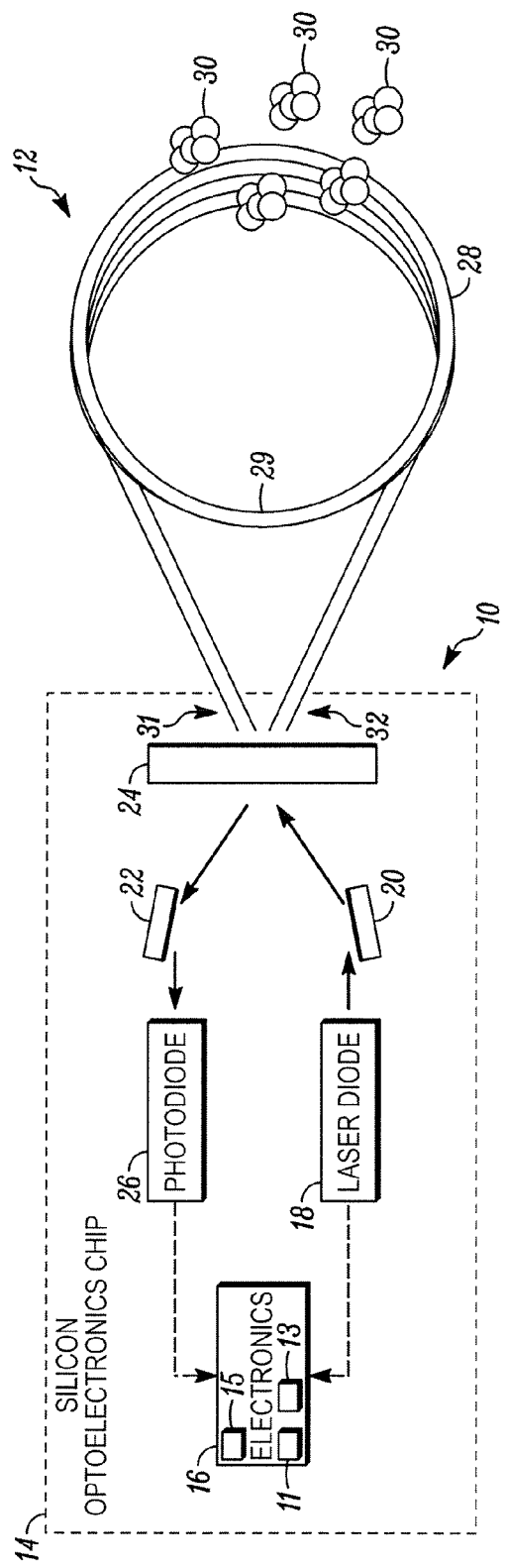
FIG. 1 is a schematic diagram of a biological agent sensor in accordance with an illustrated embodiment of the invention.

Referring now to the drawings, FIG. 1 is a schematic diagram of a biological agent sensor 10 in accordance with an exemplary embodiment of the present invention. The sensor 10 comprises a tunable coherent light source 18 (e.g., an external cavity laser diode, a DFB laser diode, etc.), a first mirror reflector 20, a recirculator 24 (e.g., a highly reflective mirror with low, but non-zero transmittance), an optical fiber coil 28 having a first end 31 receiving light from the light source 18 via the first mirror reflector 20 and recirculator 24, a second mirror reflector 22 receiving a light output from a second end of the optical fiber coil 28 via the recirculator 24, a photodetector (e.g., a photodiode) 26, and an electronics module 16 coupled to the photodetector 26 and the light source 18. The input mirror 24 and optical fiber coil 28 together form a resonator 12. The resonator 12 may have a variety of configurations, and some exemplary embodiments are described herein. The light introduced to the resonator 12 is monochromatic and circulates through multiple turns of the optical fiber coil 28 using the recirculator 24. A light output from the resonator 12 is responsive to the absence or presence of a predetermined biological agent reacted with a monoclonal antibody 30.

Figure 5:
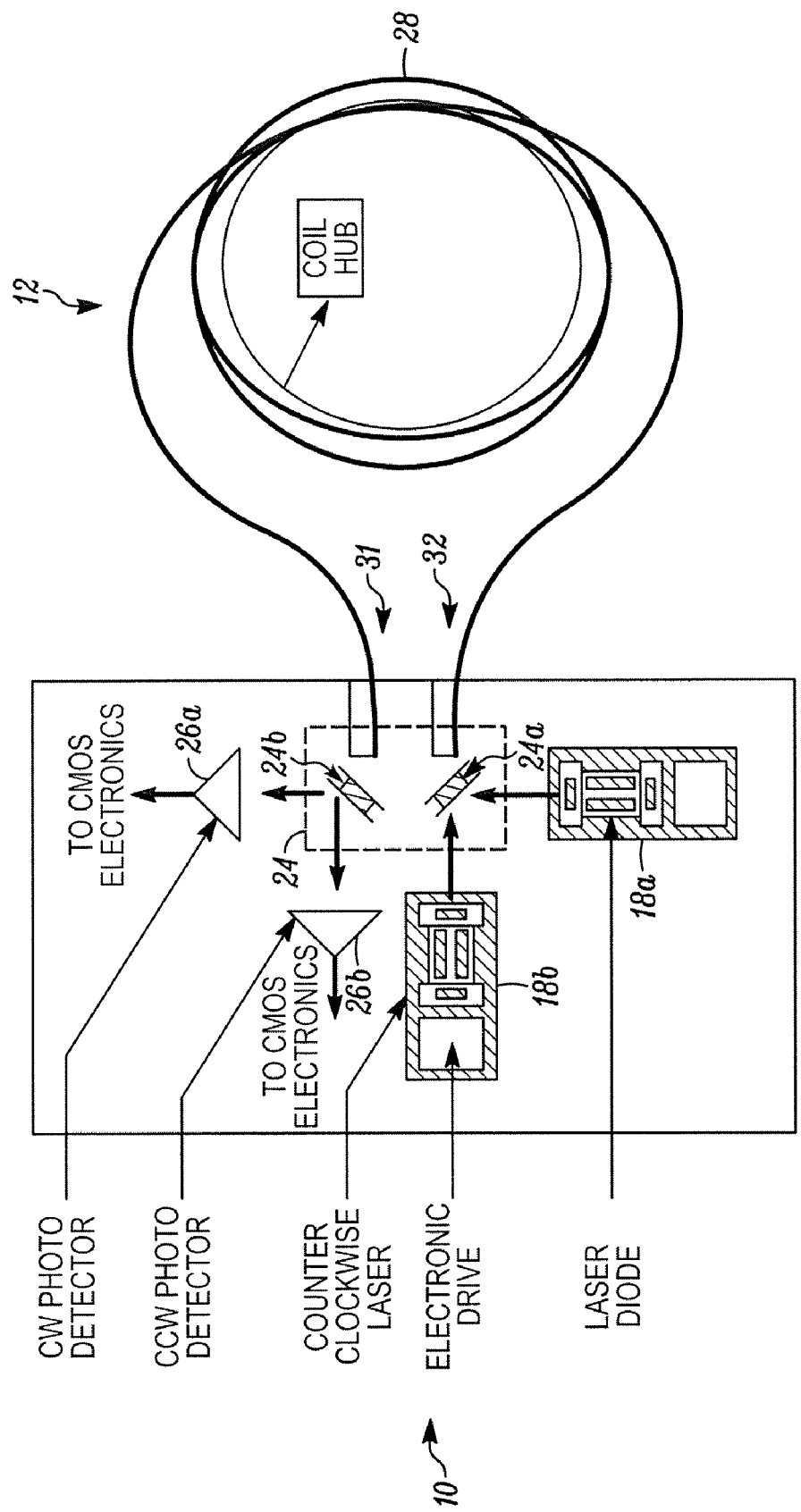
FIG. 5 is a schematic diagram of another embodiment of the sensor of the present invention.

FIG. 5 is a somewhat more complex version of FIG. 1 wherein the light may be circulated in either the clockwise (CW) or counterclockwise (CCW) direction. In FIG. 5, the recirculator 24 has been broken into two mirrors 24a and 24b that function substantially the same as the mirror 24 of FIG. 1. For purposes of simplicity, the discussion below will be directed primarily to FIG. 1.

In an exemplary embodiment, the light source 18 is a tunable laser having frequency stability, a relatively narrow line width, and a relatively high power capability. The light source 18 is tuned through, a frequency region that corresponds with the resonance frequency $f_o$ of the resonator 12 in either the CW or the CCW direction. In general, the recirculator 24 may be any optical element that reflects and reintroduces light emerging from one end of the optical fiber coil 28 into the other end of the fiber coil 28, thus causing light to propagate through the optical fiber coil 28 many times. The ability to use an input mirror instead of a fiber optic coupler for the recirculator 24 is one advantage of the sensor 10 since the mirror may be used to attenuate polarization errors and other error mechanisms, and may introduce few imperfections. However, in some cases a fiber optic coupler may be suitable.

Figure 1A:
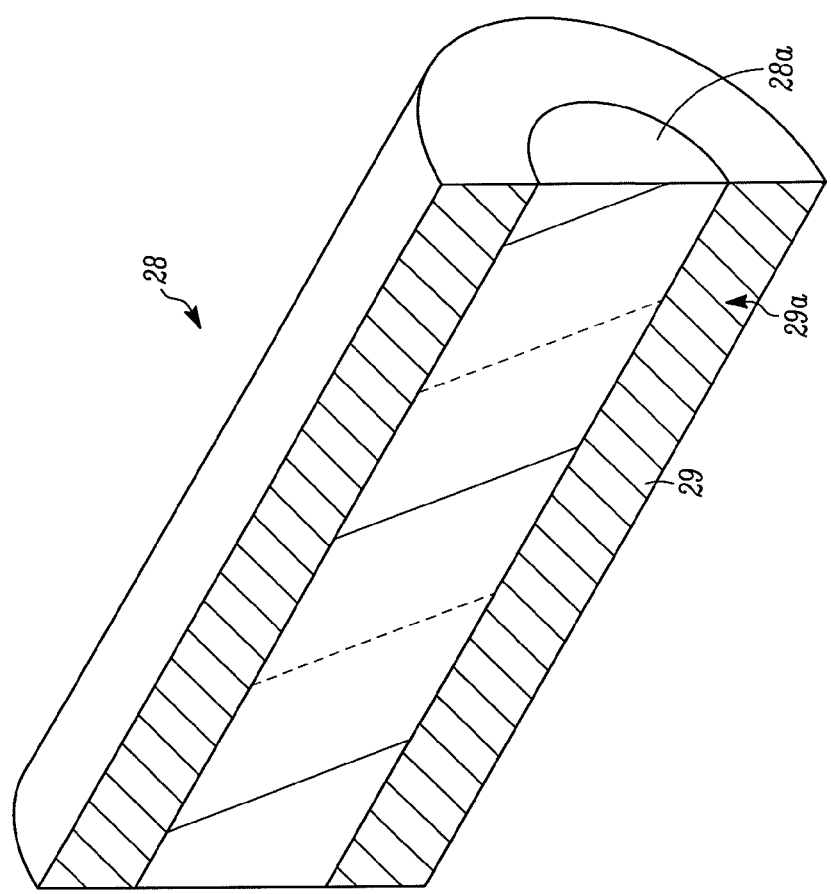
FIG. 1A is a cut-away view of an optical fiber of the sensor of FIG. 1.

In one case as shown in FIG. 1A, the optical fiber coil 28 is made of fiber whose core is typically glass based and with a cladding 29 surrounding the core that is typically polymer-based, and an indicator 29a embedded in the cladding that reacts to a predetermined biological agent 30. Another type of fiber consists of a glass core, a cladding of photonic crystalline structure, and an outer polymer based jacket, coating, or outer cladding. The indicator is contained within the outer jacket. Many polymers may be used, provided that it is possible to blend or covalently attach the monoclonal antibody to the polymer. Examples of antibody attachment technologies may include gluteraldehye or toluene diisocyanate crosslinking.

In either case, an optical fiber having an extremely low bend loss is preferably used, and the optical fiber coil 28 preferably has a relatively large number of turns about a substantially small area. For example, the coil 28 may have from about 20-40 turns of the optical fiber about a one centimeter diameter. Generally, the longer the optical path, such as provided by the optical fiber coil 28, the greater the signal-to-noise ratio of the sensor 10. To improve the signal-to-noise ratio of the sensor 10, the optical path may be increased by increasing the number of turns of the optical fiber coil 28. In the optical fiber coil 28, light introduced by the recirculator 24 traverses mostly inside the core, and only about a few percent of the optical energy of light enters the cladding of the optical fiber. The indicator may be a chemical or other substance that reacts to one or more biological substances and changes its optical characteristics for instance its color, its optical loss, or its index of refraction.

The cladding may consist of any of a variety of hydrophilic polymers. The criteria for selection of the polymers will include their durability and the ease with which they can be applied, as well as their compatibility with the method used to attach the monoclonal antibody indicator. The cladding must also have a refractive index which is lower than that of the core of the fiber in an index guided fiber. Table 1 shows a list of hydrophilic polymers, drawn from the Polymer Handbook pp. III-241-III-242, ($2^{nd}$ ed., J. Brandrup, E. H. Immergut, ed., Wiley Interscience (1975).

| Polymer | Refractive Index (Sodium D Line) |
|---|---|
| Poly vinyl ethyl ether | 1.454 |
| Poly(oxyethylene) | 1.4563 |
| Cellulose acetate butyrate | 1.46-1.49 |

-continued

| Polymer | Refractive Index (Sodium D Line) |
|---|---|
| Poly(2-methoxyethyl acrylate) | 1.463 |
| Poly(vinyl methyl ether) | 1.467 |
| Cellulose propionate | 1.47-1.49 |
| Poly(methyl acrylate) | 1.472-1.48 |
| Ethyl cellulose | 1.479 |
| Poly(vinyl butyral) | 1.48 |

It will be understood by those skilled in the art that polymers which are too soft or water soluble for use can be rendered less soluble by cross-linking, and that polymers which are not sufficiently hydrophilic can be modified by the attachment of hydrophilic side groups. Thus, polymers such as polydimethylsiloxanes, polyacrylates, polymethacrylates or polyvinyl ethers may be made more hydrophilic by attachment of groups containing hydroxy, alkyloxy, carboxylate, sulfonate, phosphate, tetraalkylammonium or other hydrophilic groups.

Polymers which have porosity in the correct pore size range will also adsorb water. The Kelvin equation (1) can be used to estimate what pore size will be required, based on the temperature and relative humidity expected. For example, if the temperature of use is expected to be near 25° C., with a relative humidity of 50%, we can calculate that the desired pore size will be near 15 nm.

$$\ln\left(\frac{P}{P_0}\right) = \frac{-2\gamma V_L}{RTr_m} \quad (1)$$

γ=surface tension of water (72 dyne/cm)

$V_L$=molar volume of water (18 g/cc)

R=gas constant

T=temperature

P=vapor pressure of water $P_0$=saturation vapor pressure of water

Biological materials to be detected using this invention may include viruses, bacteria, spores, fungi, proteins, polysaccharides or any other biological material. Indicators for these materials may include other biological materials capable of recognizing the specific organisms to be detected, but not other organisms. One such method of recognition may be the use of antibodies covalently bound to the polymer which bind to the biological material. These antibodies will result in a change of refractive index when they have bound the target antigen.

In operation, light produced by the light source 18 is directed to the first mirror reflector 20 which in turn directs this light to the recirculator 24. Light from the light source 18 is scanned (swept) through the resonance frequency of the resonator (which is comprised of the optical fiber coil 28 and the recirculator 24), in a corresponding direction (e.g., the clockwise direction) of propagation, a first portion of which is transmitted through the recirculator 24 and into the first end 31 of the optical fiber coil 28. A second portion, i.e. the reflected portion, is reflected from the recirculator 24 to mirror 22. The resonance frequencies for each of the CW and CCW paths through the optical fiber coil 28 are based on a constructive interference of successively circulated beams in each optical path. After the first portion of light propagates through the core of the optical fiber coil 28, the light emerges from the second end 32 of the optical fiber coil 28. In this exemplary embodiment, the light emerging from the second end 32 is directed to the recirculator 24. A portion of this light is reflected back into the first end 31, by the recirculator 24 while another portion is transmitted (i.e., the transmitted wave) to the second mirror reflector 22. The transmitted wave is a fraction of (and is derived from) the recirculating light wave inside the resonator 12. The transmitted wave and the reflected wave are directed, via the second mirror reflector 22 to the photodetector 26 where they are interfered (i.e., interference occurs between the transmitted and reflected waves). As the frequency of the light is detuned well away from resonance, the transmitted portion is very small and only the reflected portion impinges on the photodetector, indicating a maximum intensity, and very little destructive interference. As the frequency is scanned through the center of the resonance, the transmitted wave is maximized, producing maximum destructive interference with the reflected wave, and therefore providing a resonance dip whose minima is indicative of the resonance center.

To observe the resonance center-frequency of the resonator (consisting of optical fiber coil 28 and recirculator 24) 12, in either the CW or CCW direction, the light intensity detected by the photodetector can be measured or a standard synchronous-detection technique (phase sensitive detection) may be used. Detection may be accomplished by sweeping the frequency of the light source 18 through a frequency range while detecting the light output via the photodetector 26. In the case of synchronous detection, the input light beam is sinusoidally frequency modulated (at a rate much higher than the sweep rate) by the controller 16 at a frequency ($f_m$) to dither the input beam frequency across the resonance lineshape while resonance is measured on the photodetector 26 (via sweeping of the frequency). For example, the electronic module 16 may sweep the input light beam across a frequency range via a controlling signal to the light source 18 while demodulating the output of the photodetector 26 at $f_m$ to measure resonance via the light output of the circulating light beam. At a line center of the resonance lineshape, or the resonance center, the photodetector 26 detects a minimum output at the fundamental detection frequency $f_m$ and detects a maximum near the points of highest slope on either side of the lineshape. When the frequency is well off-resonance, an intensity signal maximum is observed, but the signal at $f_m$ is substantially zero. To observe the linewidth of the resonance lineshape, the laser frequency is scanned such that the light intensity signal of the photodetector 26 at least goes through a sequence of observing a half maximum, then the minimum, then another half maximum, all as the laser frequency is scanned monotonically (i.e., swept through the frequency range near $f_o$). The linewidth is determined by the frequency separation between half maxima.

Alternatively a measure of the lineshape width may be determined by monitoring the frequency difference between maxima of the demodulated signal at $f_m$, as the laser frequency is scanned monotonically across the lineshape. In this case, a measurement of the frequency width of the resonance between points of highest slope is proportional to the resonator linewidth, and thus the loss of the resonator. The laser frequency excursion from half-maximum intensity to half maximum intensity (or between points of highest slope) is the resonator linewidth (or proportional to the resonator linewidth), which is indicative of the loss within the fiber coil 28, and hence, is a measure of the presence of the biological substance. Widening of the linewidth represents the presence of the subject substance, in the case of an increased-loss measurement. The laser frequency excursion is measured by recording the laser frequency difference between the time that the detector observes a half-maximum signal and the time the detector observes the second half-maximum signal. The laser frequency at each of those two points in time may be measured directly or indirectly. One direct measure involves beating its frequency with another laser that is not being scanned and measuring the beat frequency difference between the two points in time. An indirect, and perhaps less expensive way is to precalibrate the laser frequency versus the electrical signal input used to scan the laser. The calibrated values may be saved in a lookup table 11 within a memory of the controller 16. This may be a current drive signal that changes the injection current of the laser, a current drive signal to a thermoelectric cooler that changes the temperature of the laser, or a voltage drive signal to a piezoelectric transducer that changes the pathlength of the laser cavity to change its frequency. In either of these cases, the laser frequency shift versus the magnitude of the drive signal can be factory-calibrated, which allows the drive signal excursion to be used as a measure of the frequency excursion during operation.

When the light source 18 is tuned away from the resonance frequency of the resonator 12 in the CW direction, for example, the energy from the CW beam does not enter the optical fiber and the light is reflected off the highly reflective mirror of the recirculator 24 to produce a maximum intensity at the photodetector 26. When the light source 18 is tuned at the resonance frequency of the resonator 12 in the CW direction, the CW beam enters the optical fiber coil 28, and the light striking the photodetector 26 has a minimum output thereby indicating the resonance center. Similarly, if the device were to inject light into the CCW direction instead, the CCW beam enters the optical fiber coil 28 when the CCW beam is tuned to the resonance frequency of the resonator 12 in the CCW direction.

When the biological agent 30 is present within the optical fiber coil 28, the indicator embedded in the cladding of the optical fiber coil 28 is expected to react (e.g., bind) with the biological agent 30 and alter the optical properties of the optical fiber coil 28. For example the altered optical properties of the optical fiber coil 28 may include, but are not necessarily limited to, a change in the index of refraction or an increase or decrease in the optical absorbance or loss of the optical fiber coil 28.

In order to scan the resonant frequency of the resonator 12, a driver controller 13 may sequentially select a predetermined set or range of current values relating to the resonance frequency $f_o$ and step the laser diode 18 through those values. For example, the resonator 12 in an uncontaminated state may have half maximum optical energy output values (as measured by the diode 26) at resonant frequency values equal to $f_o +/- \Delta f$, and with the biological contaminant the half maximum resonant frequency values may be $f_o +/- 5\Delta f$. In this case, the predetermined set of current values would have a maximum current value $x_1$ and a minimum current value $x_2$ that correspond to $f_o + 5\Delta f$ and $f_o - 5\Delta f$, respectively. If the driver controller 13 were to step from the minimum current value to the maximum current value in twenty equal steps then the first current value applied to the laser diode 18 would be $x_2$ and the increment in current value for each step would be $(x_1 - x_2)/20$. In this case, the first current value would be $x_2$, the second value would be $x_2 + (x_1 - x_2)/20$, the third value would be $x_2 + 2(x_1 - x_2)/20$, and so on. The current could also be tuned continuously, with a continuous function being stored in the processor.

The one-half maximum values on either side of resonant frequency $f_o$ may be detected by the photodetector 26 and correlated to light source current values. In this case, the predetermined set of current values may extend over some larger current range determined by the changes to the resonant frequency caused by the presence of the biological material. If the change in resonant frequencies caused by the presence of the biological material causes one-half maximum values of the resonant frequency $f_o$ to spread out by a factor of five, then the predetermined current range may correspond to 5 times the one-half maximum values of the resonator 12 in the uncontaminated state.

In one illustrated embodiment, the lookup table 11 may contain a list of current values and the respective frequencies that corresponds to those current values. The lookup table 11 may also contain a number of frequency signatures. A frequency signature in this case means a set of frequencies of the light source 18 and a corresponding value that is to be detected by the photodetector 26. A first reference signature may be provided within the lookup table 11 for the resonator in an uncontaminated state and one or more other contamination or biological agent signatures may be provided within the lookup table 11 for the resonator 12 in different degrees of the contaminated state. In use, the controller 16 continually collects test signatures by causing the light source 18 to scan through the predetermined set of frequencies while collecting a respective light value from the photodetector 26. The test signature is compared with the reference and contamination signatures within a comparator 15. When the comparator 15 detects a match between the test signature and a contamination signature, the controller 16 activates an alarm.

In an exemplary embodiment, the sensor 10 can be constructed on a silicon-based micro-optical bench 14 that integrates electronics (e.g., the electronic module 16) and optics and provides an efficient and expedient interface between the two. Miniature optical components having a feature size of as little as 10 microns, such as the mirror reflectors 20, 22 and the recirculator 24, may be mounted on silicon surfaces to eliminate large bulk optics, even though the light wave may be traveling in free space. Some of these optical functions may also be embedded in waveguides residing in the silicon material. In this exemplary embodiment, the light source 18 and related frequency tuning components and the photodetector 26 may also be mounted on the optical bench. The use of these techniques allows the fabrication of optics in or on a silicon platform and thus integrated of the optics with the electronics. The light source itself may be a compound structure on which several components may be mounted, or formed on the micro-optical bench 14. For instance, it may be an external cavity laser diode, where the laser diode is placed between two reflective surfaces which are either formed or placed on the substrate. There may also be frequency selective intra-cavity elements formed or placed within the laser cavity to make it a single frequency laser, such as a grating or an etalon. There may also be elements included with laser source 18 that are mounted or formed external to the laser cavity that are used to shape or collimate the laser beam, such as lenses.

Figure 2:
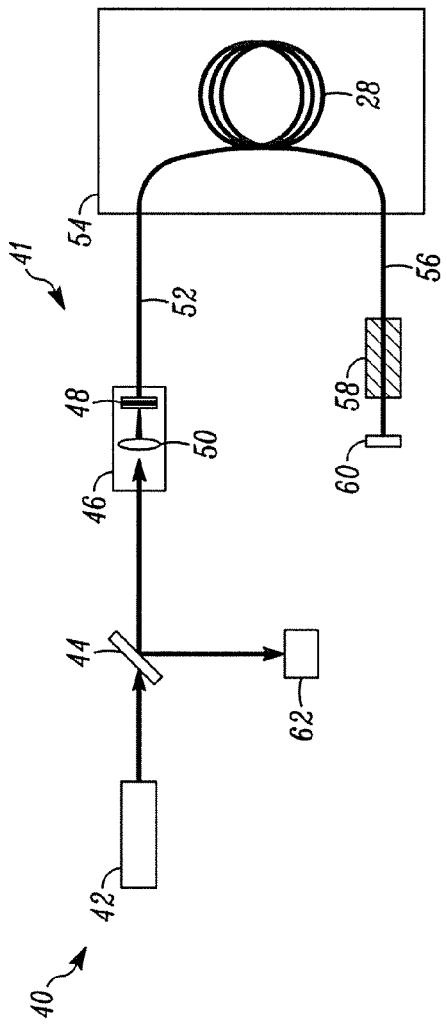
FIG. 2 is a schematic diagram of a biological agent sensor having a linear resonator in accordance with another exemplary embodiment of the present invention.

FIG. 2 is a schematic diagram of a biological agent sensor 40 having a linear resonator 41 in accordance with another exemplary embodiment of the present invention. The sensor 40 comprises a tunable laser (e.g., a He—Ne laser, or an external cavity laser diode, each with a built-in isolator) 42 that synthesizes an input light beam and introduces the input light beam into the linear resonator 41. The sensor 40 comprises a beam splitter (e.g., a 50-50% beam splitter) 44, an input element 46, the optical fiber coil 28, and output mirror 60, and a photodetector 62. The input element 46 includes, but is not necessarily limited to, an input mirror 48 (e.g., a 95-5% mirror) although a fiber grating may be substituted for the input mirror 48. Additionally, the input element 46 may include optics 50 for directing the light from the beam splitter 44 to a first end 52 of the optical fiber coil 28 and for directing light from the same end 52 of the optical fiber coil 28 and for directing light from the same end 52 of the optical fiber coil 28 to the beam splitter 44. The optical fiber coil 28 is housed in a permeable package 54 for detecting the predetermined biological agent (e.g., associated with the indicator embedded in the optical fiber coil 28). The linear resonator 41 is formed by reflector 48, fiber coil 28 and reflector 60. Reflectors 48 and 60 may be formed or deposited directly onto the fiber tips or fiber ends 52 and 56 to achieve a low loss resonator.

A modulator (e.g., a piezoelectric transducer) 58 may be coupled to the optical fiber coil 28 to modulate the pathlength of the light (e.g., sinusoidal modulation) circulating through the optical fiber coil 28 during resonance linewidth determination so that synchronous detection may be used. For example, the input light beam produced by the laser 42 is scanned through the resonance frequency $f_o$ of the resonator and the modulator 58 sinusoidally modulates the pathlength of the light circulating through the optical fiber coil 28. In another exemplary embodiment, the modulator 58 is omitted when the laser 42 has frequency modulation capabilities incorporated therewith. In a third exemplary embodiment, the laser frequency is fixed, and both the frequency scanning and the modulation are effected by the modulator 58. In this latter case, the resonator resonance frequency is scanned through the region of the laser frequency, which is equivalent, in principle, to scanning the laser frequency across a fixed resonance frequency of the fiber resonator.

The input light beam from the laser 42 is directed by the beam splitter 44 to the input element 46 which directs the input light beam to the first end 52 of the optical fiber coil 28. When tuned to the resonance frequency associated with the resonator 41 containing the optical fiber coil 28, a majority of the input light beam energy enters the optical fiber coil 28. During each round-trip of light propagation in the resonator, the light propagates through the optical fiber coil 28 in the forward direction, emerges from the second end 56 of the optical fiber coil 28 and impinges on the output mirror 60 which reflects the light back into the optical fiber coil 28 at the second end 56. A light output is produced from the light propagating back and forth in the optical fiber coil 28 at the first end 52 of the optical fiber coil 28 which is directed by the input element 46 to the beam splitter 44. The beam splitter 44 reflects a portion of the light output to the photodetector 62, which may be coupled to electronics (similar to FIG. 1). Alternatively, mirror 60 may be a partially transmitting mirror and the photo-detector 62 may be positioned to receive light emanating from the resonator, and thus, monitor resonance.

Figure 3:
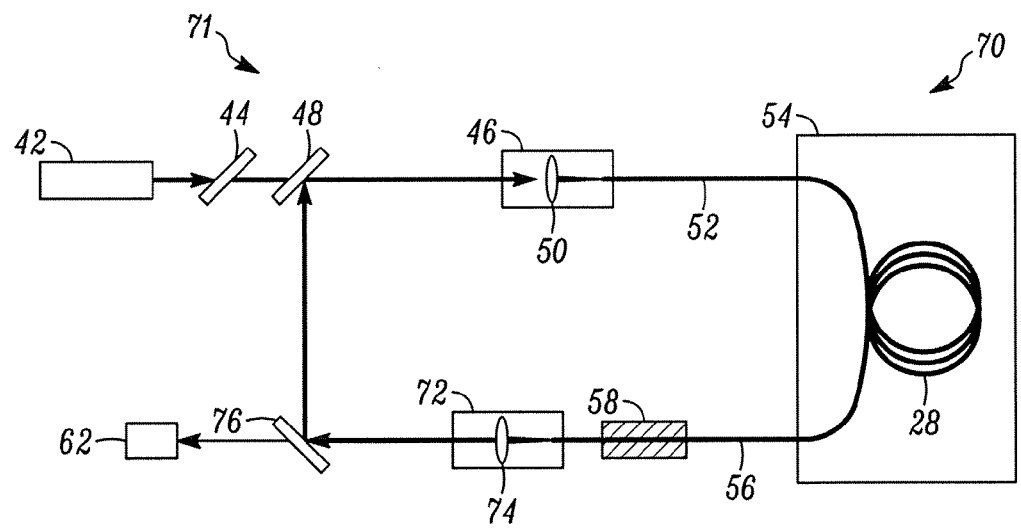
FIG. 3 is a schematic diagram of a biological agent sensor having a ring resonator in accordance with another illustrated embodiment of the invention.

FIG. 3 is a schematic diagram of the biological agent sensor 70 having a ring resonator 71 in accordance with another exemplary embodiment of the present invention. In this exemplary embodiment, the laser 42 introduces the input light beam into the ring resonator 71. The biological agent sensor 70 comprises a laser 42, the input mirror 48, an input element 46, the optical fiber coil 28, an output element 72, an output mirror 76, and a photodetector 62. The optical fiber coil 28 is housed in the permeable or semi-open package 54, and the modulator (e.g., a piezoelectric transducer) 58 may be coupled to the optical fiber coil 28 to modulate the light path (e.g., sinusoidal modulation and/or resonance frequency scanning) circulating through the optical fiber coil 28 during resonance linewidth determination. The resonator comprises, at mirror 48 and 76, a fiber coil 28, input element 46 and output element 72. In another embodiment, mirrors 48 and 76 are designated with sufficient curvature to eliminate input element 46 and output element 72. In yet another embodiment the two mirrors 48 and 76 and the input element 46 and output element 72 are replaced with a fiber optic coupler which is spliced to the coil 28.

The input light beam from the laser 42 is directed to the input mirror 48 which transmits a portion of the input light beam to the input element 46. The input element 46 directs light from the input mirror 48 to the first end 52 of the optical fiber coil 28. When tuned to the resonance frequency of the resonator, a majority of the input light beam enters the first end 52 of the optical fiber coil 28. After propagating through the optical fiber coils 28, light emerges from the second end 56 of the optical fiber coil 28 and is directed to the output element 72. The output element 72 may include optics 74 for directing light from the second end 56 of the optical fiber coil 28 to the output mirror 76. The output mirror 76 reflects the light from the output element 72 to the input mirror 48, and input mirror 48 directs a majority of this to the input element 46 to complete the resonator optical path. A light output is produced from the light circulating around the optical path, including the optical fiber coil 28, at the output mirror 76 which passes a small fraction of the light that is circulating within the resonator out to the photodetector 62.

Figure 4:
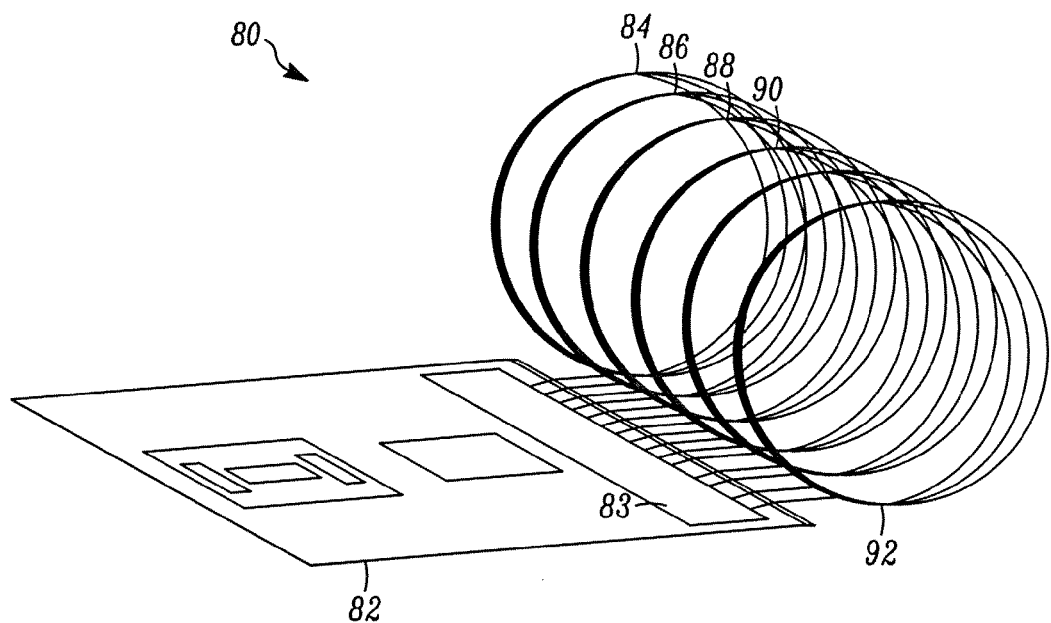
FIG. 4 is a schematic diagram of a multiplexed biological agent sensor in accordance with an illustrated embodiment of the invention.

FIG. 4 is a schematic diagram of a multiplexed biological agent sensor 80 in accordance with another exemplary embodiment of the present invention. The sensor 80 comprises a silicon-based micro-optical bench 82 and a multiple optical fiber coils 84, 86, 88, 90, 92 coupled to the micro-optical bench 82. The micro-optical bench 82 integrates electronics (e.g., the electronics module 16 shown in FIG. 1) and optics (e.g., the beam splitter 44, input and output mirrors 48, 60, 76, input and output elements 46, 72, and photodetector 62 shown in FIGS. 2 and 3). For example, the electronics module 16, photodetector 26, light source 18, mirror reflectors 20, 22, and input mirror 24 shown in FIG. 1 may be integrated with the micro-optical bench 82. The sensor 80 additionally includes, but is not necessarily limited, a multiplexer 83 formed on the micro-optical bench 82 is coupled (e.g., via one or more fiber vee-grooves and/or input mirrors) to each of the optical fiber coils 84, 86, 88, 90, 92.

In the exemplary embodiment, the multiplexer 83 directs input light beams to each of the optical fiber coils 84, 86, 88, 90, 92 and receives output light beams from the optical fiber coils 84, 86, 88, 90, 92 having circulated through each of the optical fiber coils 84, 86, 88, 90, 92. The output light beams are each directed to one or more input mirrors to produce a light output, from which a resonance lineshape may be determined, and may be directed back to the corresponding optical fiber coil to complete a resonator optical path. The input light beams are each scanned across to the resonance frequency of the corresponding optical fiber coil 84, 86, 88, 90, 92. As previously described, this may be accomplished by having a fixed average input light frequency and scanning the length of each of the resonator pathlengths, thus scanning through the resonance lineshape. Each of the optical fiber coils has an indicator embedded therein that reacts to a different biological agent. Using the sensor 80, multiple biological agents may be detected using a single device with a common output interface and possibly a wireless transmitter.

The invention claimed is:

1. A biological agent detector for detecting predetermined biological agents comprising:
    an optical fiber resonator containing an optical fiber;
    a cladding that blends with or covalently attaches a bioindicator and clads the majority of the length of the optical fiber;
    a coherent light source that sweeps through a predetermined optical frequency range to excite the optical fiber; and
    a biological agent signature detector that detects a biological agent based upon a change in a resonance characteristic of the optical fiber resonator to the swept optical frequency range at a plurality of frequencies caused by absorption of the predetermined biological agent into the cladding of the fiber.

2. The biological agent detector as in claim 1 wherein the coherent light source further comprises a DFB laser.

3. The biological agent detector as in claim 2 wherein the biological agent signature detector further comprises a photodiode.

4. The biological agent detector as in claim 2 wherein the biological agent signature detector further comprises monoclonal antibodies.

5. The biological agent detector as in claim 3 wherein the biological agent signature detector further comprises a laser controller coupled to the DFB laser that sweeps a junction current of the DFB laser through a predetermined current range.

6. The biological agent detector as in claim 5 wherein the biological agent signature detector further comprises a laser look up table that correlates current values within the predetermined current range with lasing frequencies of the DFB laser.

7. The biological agent detector as in claim 6 wherein the laser lookup table further comprises a first junction current difference value that corresponds to a calibration value and to a resonance lineshape width or free spectral of the optical fiber before being exposed to any biological agents.

8. The biological agent detector as in claim 7 wherein the biological agent signature detector further comprises a biological agent signature look up table that contains a resonance line shape linewidth or free spectral range for at least some dosage of a predetermined biological agent.

9. The biological agent detector as in claim 8 wherein the biological agent signal detector further comprises a comparator that detects a resonance of the optical fiber resonator by comparing an output of the photodiode with a resonance threshold value.

10. The biological agent detector as in claim 9 wherein the biological agent signature detector further comprising a processor that generates a frequency sweep of the DFB laser.

11. The biological agent detector as in claim 10 wherein the range of the frequency sweep comprises at least one free spectral range of the resonator.

12. The biological agent detector as in claim 8 wherein said change in resonance characteristic is a frequency difference between resonances.

13. The biological agent detector as in claim 8 said change in resonance characteristic is a difference in a resonance linewidth or finesse.

14. The biological agent detector as in claim 1 wherein the cladding is a polymer that blends with or is chemically covalently attached with a bioindicator and dads a majority of the length of the fiber.

15. The biological agent detector as in claim 14 wherein the cladding is a polymer selected from the group consisting of crosslinked chitosan materials, polysaccharides, hydroxy substituted acrylate coatings and Nafion®.

16. The biological agent detector as in claim 1 wherein the cladding is a hygroscopic gel that blends with or covalently attaches a bioindicator and dads the majority of the length of the fiber.

17. A method for detecting predetermined biological agents comprising:
- providing an optical fiber resonator having an optical fiber with a cladding that blends with or covalently attaches a bioindicator and dads the majority of the length of the optical fiber;
- providing a coherent light source that excites the optical fiber resonator;
- sweeping the light source though a predetermined optical frequency range; and
- providing detection of a biological agent upon the light source exciting the optical fiber resonator based upon a change in a resonance characteristic of the optical fiber resonator to the swept frequency range at a plurality of frequencies caused by absorption of the predetermined biological agent into the cladding of the fiber.

18. The method as in claim 17 wherein the cladding is a polymer that blends with or covalently attaches the bioindicator and dads the optical fiber.

19. The method as in claim 18 wherein the cladding is a hygroscopic gel that blends with or covalently attaches the bioindicator and dads the optical fiber.

20. The method as in claim 17 wherein the optical fiber is a photonic crystal fiber.

* * * * *